(12) United States Patent
Deane et al.

(10) Patent No.: US 8,425,965 B2
(45) Date of Patent: Apr. 23, 2013

(54) METHOD FOR HEATING OR STERILIZING A LIQUID STREAM

(75) Inventors: Geoffrey F. Deane, Bellevue, WA (US); William Gates, Redmond, WA (US); Roderick A. Hyde, Redmond, WA (US); Jordin T. Kare, Seattle, WA (US); Nathan P. Myhrvold, Bellevue, WA (US); David B. Tuckerman, Lafayette, CA (US); Lowell L. Wood, Jr., Bellevue, WA (US); Ozgur Yildirim, Bellevue, WA (US)

(73) Assignee: Tokitae LLC

( * ) Notice: Subject to any disclaimer, the term of this patent is extended or adjusted under 35 U.S.C. 154(b) by 258 days.

(21) Appl. No.: 12/462,200

(22) Filed: Jul. 29, 2009

(65) Prior Publication Data
US 2011/0027441 A1     Feb. 3, 2011

(51) Int. Cl.
*A23C 3/02*     (2006.01)

(52) U.S. Cl.
USPC ............................ 426/520; 426/521; 426/522

(58) Field of Classification Search .................. 426/231, 426/520–522
See application file for complete search history.

(56) References Cited

U.S. PATENT DOCUMENTS

| | | | | |
|---|---|---|---|---|
| 2,001,849 A | * | 5/1935 | Olsen ............................ | 165/78 |
| 2,148,100 A | * | 2/1939 | Browne ......................... | 426/423 |
| 2,270,540 A | * | 1/1942 | Mallory ........................ | 426/521 |
| 2,937,856 A | * | 5/1960 | Thomson ...................... | 165/66 |
| 3,041,046 A | * | 6/1962 | Nellis, Jr. et al. ............. | 165/234 |
| 3,228,465 A | * | 1/1966 | Vadot ............................ | 165/167 |
| 4,313,370 A |  | 2/1982 | Skoli et al. | |
| 4,380,166 A |  | 4/1983 | Crombie | |
| 4,446,778 A | * | 5/1984 | Cipelletti ...................... | 99/455 |
| 4,534,986 A | * | 8/1985 | Hasting ......................... | 426/521 |
| 4,541,040 A |  | 9/1985 | Allfather | |
| 4,542,034 A |  | 9/1985 | Aule et al. | |
| 4,610,298 A |  | 9/1986 | van Schagen et al. | |
| 4,752,487 A | * | 6/1988 | Collyer et al. ................ | 426/231 |
| 4,781,244 A |  | 11/1988 | Kuramitsu et al. | |
| 4,854,377 A |  | 8/1989 | Komoto et al. | |
| 4,876,100 A |  | 10/1989 | Holm et al. | |
| 4,901,908 A |  | 2/1990 | Negura et al. | |

(Continued)

FOREIGN PATENT DOCUMENTS

| | | |
|---|---|---|
| CN | 2661189 Y | 12/2004 |
| CN | 1889256 A | 1/2007 |
| EP | 0 722 075 B1 | 7/1995 |
| WO | WO 99/15638 | 4/1999 |

OTHER PUBLICATIONS

PCT International Search Report; International App. No. PCT/US 10/02123; bearing a date of Sep. 30, 2010; pp. 1-2.
PCT International Search Report; International App. No. PCT/US 10/02125; bearing a date of Sep. 23, 2010; pp. 1-2.

(Continued)

*Primary Examiner* — Drew E Becker

(57) ABSTRACT

A method of sterilizing a liquid food product includes flowing a food product to be sterilized through an input channel. The method also includes flowing the liquid food product through a heating channel that is fluidly coupled to the input channel. Further, the method includes flowing the food product through an output channel fluidly coupled to the heating channel. The output channel is adjacent the input channel, and the output channel, the input channel, and the heating channel are all integrated portions of a heat exchanger. Further still, the method includes transferring heat between the output channel and the input channel.

36 Claims, 12 Drawing Sheets

U.S. PATENT DOCUMENTS

| | | | |
|---|---|---|---|
| 4,997,662 A * | 3/1991 | Lidman et al. | 426/231 |
| 5,054,385 A | 10/1991 | Scheel et al. | |
| 5,360,055 A | 11/1994 | Hup et al. | |
| 5,403,564 A * | 4/1995 | Katschnig et al. | 422/307 |
| 5,429,177 A | 7/1995 | Yaron et al. | |
| 5,511,613 A * | 4/1996 | Mohn et al. | 165/177 |
| 5,829,224 A | 11/1998 | Sizer | |
| 5,846,583 A | 12/1998 | Gentner | |
| 5,866,804 A | 2/1999 | O'Keeffe | |
| 5,962,288 A | 10/1999 | Aksenov et al. | |
| 5,972,405 A | 10/1999 | Sizer | |
| 6,126,723 A | 10/2000 | Drost et al. | |
| 6,250,379 B1 * | 6/2001 | Geissler et al. | 165/158 |
| 6,277,610 B1 | 8/2001 | Grae | |
| 6,344,229 B2 * | 2/2002 | Schubert et al. | 426/521 |
| 6,410,284 B1 | 6/2002 | Aksenov et al. | |
| 6,460,348 B2 | 10/2002 | Okamura et al. | |
| 6,488,076 B1 | 12/2002 | Yasuda et al. | |
| 6,521,133 B1 | 2/2003 | Roediger | |
| 6,555,055 B1 | 4/2003 | Cisar et al. | |
| 6,579,706 B2 | 6/2003 | Grae | |
| 6,599,546 B2 * | 7/2003 | Palaniappan | 426/231 |
| 6,742,576 B2 | 6/2004 | Bergevin | |
| 6,793,831 B1 | 9/2004 | Paul et al. | |
| 6,863,805 B1 | 3/2005 | Barreras, Sr. et al. | |
| 6,881,816 B2 | 4/2005 | Gharda et al. | |
| 6,921,518 B2 | 7/2005 | Johnston | |
| 6,955,340 B2 * | 10/2005 | Palm | 261/62 |
| 6,976,347 B2 | 12/2005 | Karman et al. | |
| 7,033,553 B2 | 4/2006 | Johnston et al. | |
| 7,037,694 B2 | 5/2006 | Aksenov et al. | |
| 7,156,159 B2 | 1/2007 | Lovette et al. | |
| 7,172,735 B1 | 2/2007 | Lowe et al. | |
| 7,174,954 B1 | 2/2007 | Schwartz et al. | |
| 7,185,697 B2 | 3/2007 | Goodson et al. | |
| 7,186,430 B2 * | 3/2007 | Feldmeier | 426/521 |
| 7,219,712 B2 | 5/2007 | Qiu et al. | |
| 7,220,365 B2 | 5/2007 | Qu et al. | |
| 7,226,207 B2 | 6/2007 | Feldmeier | |
| 7,449,314 B2 | 11/2008 | Grae | |
| 7,601,377 B2 | 10/2009 | Aksenov et al. | |
| 7,708,941 B2 | 5/2010 | Arofikin | |
| 2003/0049356 A1 | 3/2003 | Mielsen et al. | |
| 2003/0066638 A1 | 4/2003 | Qu et al. | |
| 2003/0124366 A1 | 7/2003 | Carroll et al. | |
| 2003/0175394 A1 * | 9/2003 | Modler | 426/522 |
| 2003/0221438 A1 | 12/2003 | Rane et al. | |
| 2004/0055737 A1 | 3/2004 | Mitchell | |
| 2004/0187707 A1 | 9/2004 | Nielsen et al. | |
| 2005/0087767 A1 | 4/2005 | Fitzgerald et al. | |
| 2005/0112257 A1 | 5/2005 | Feldmeier | |
| 2005/0129580 A1 * | 6/2005 | Swinehart et al. | 422/100 |
| 2005/0232861 A1 | 10/2005 | Buchanan et al. | |
| 2006/0029704 A1 | 2/2006 | Karman et al. | |
| 2006/0033674 A1 | 2/2006 | Essig, Jr. et al. | |
| 2006/0102328 A1 | 5/2006 | Toyama et al. | |
| 2006/0118273 A1 | 6/2006 | Qiu et al. | |
| 2006/0201163 A1 | 9/2006 | Haefner et al. | |
| 2006/0231233 A1 | 10/2006 | Farid et al. | |
| 2006/0254759 A1 | 11/2006 | Johnston | |
| 2008/0181833 A1 | 7/2008 | Lawal et al. | |
| 2008/0210402 A1 | 9/2008 | Kidwell et al. | |
| 2008/0277095 A1 | 11/2008 | Zhai | |
| 2009/0211977 A1 * | 8/2009 | Miller | 210/646 |

OTHER PUBLICATIONS

MST—Millesecond Technologies Home Page; bearing a date of 2002-2008, printed Jul. 24, 2012; p. 1; located at: http://millisecworldwide.com/index.htm.

Millesecond Technologies Co., Ltd. Home Page; printed on Sep. 24, 2012; p. 1; located at: http://millisec.ru/indexen.shtml.htm.

"Regenerative heat exchanger"; Wikipedia; Jul. 24, 2012; pp. 1-4; located at http://en.wikipedia.org/wiki/Regenerative_heat_exchanger.

* cited by examiner

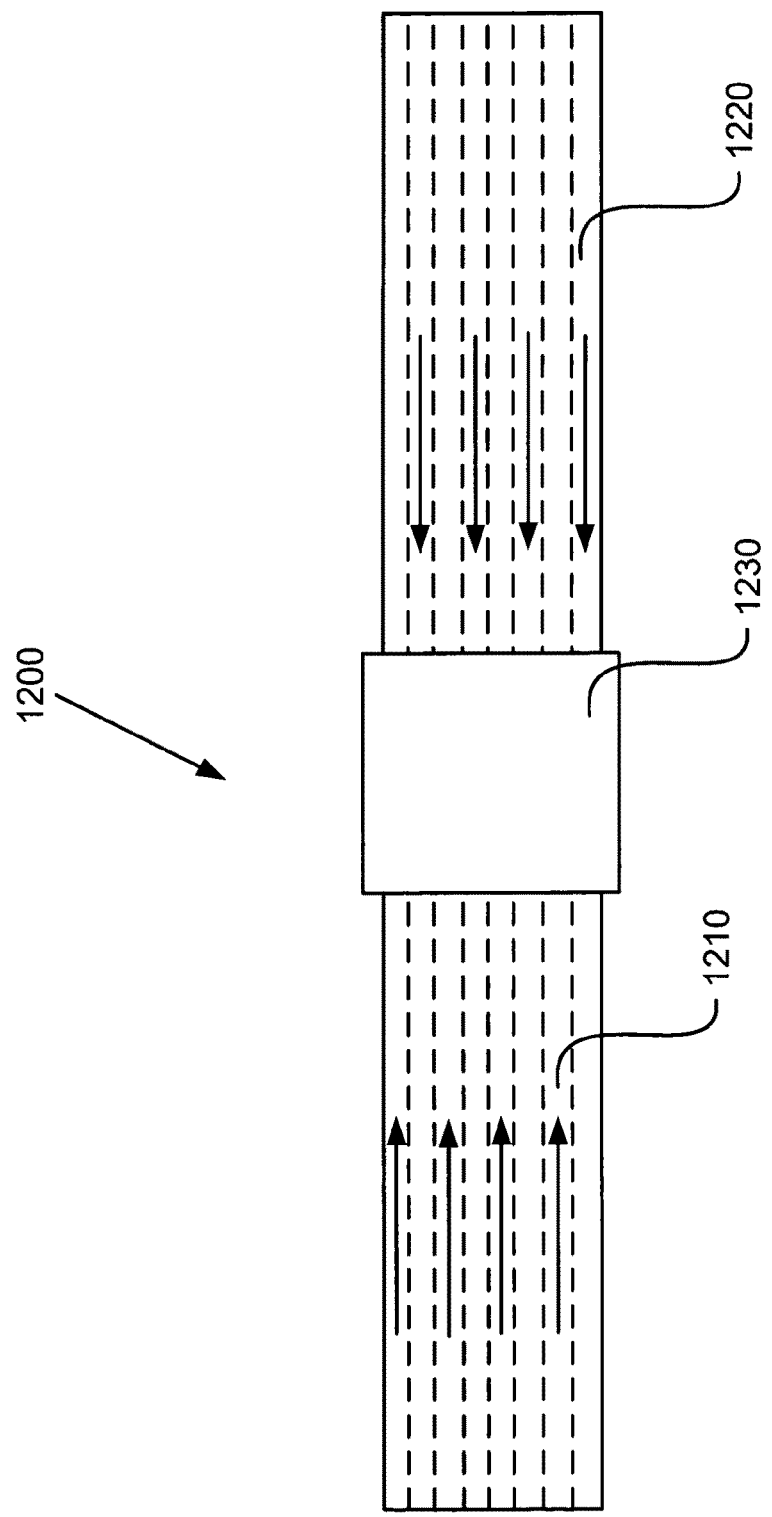

METHOD FOR HEATING OR STERILIZING A LIQUID STREAM

CROSS-REFERENCE TO RELATED APPLICATIONS

The present application is related to and claims the benefit of the earliest available effective filing date(s) from the following listed application(s) (the "Related Applications") (e.g., claims earliest available priority dates for other than provisional patent applications or claims benefits under 35 USC §119(e) for provisional patent applications, for any and all parent, grandparent, great-grandparent, etc. applications of the Related Application(s)).

RELATED APPLICATIONS

1. For purposes of the USPTO extra-statutory requirements, the present application relates to U.S. patent application Ser. No. 12/462,213, entitled A SYSTEM AND STRUCTURE FOR HEATING OR STERILIZING A LIQUID STREAM, naming Geoffrey F. Deane, William Gates, Roderick A. Hyde, Jordin T. Kare, Nathan P. Myhrvold, David B. Tuckerman, Lowell L. Wood, Jr. and Ozgur Yildirim as inventors, filed contemporaneously herewith, which is currently co-pending, or is an application of which a currently co-pending application is entitled to the benefit of the filing date.
2. For purposes of the USPTO extra-statutory requirements, the present application relates to U.S. patent application Ser. No. UNKNOWN 12/462,206, entitled PASTEURIZATION SYSTEM AND METHOD, naming Geoffrey F. Deane, William Gates, Roderick A. Hyde, Jordin T. Kare, Nathan P. Myhrvold, David B. Tuckerman, Lowell L. Wood, Jr. and Ozgur Yildirim as inventors, filed contemporaneously herewith, which is currently co-pending, or is an application of which a currently co-pending application is entitled to the benefit of the filing date.

The United States Patent Office (USPTO) has published a notice to the effect that the USPTO's computer programs require that patent applicants reference both a serial number and indicate whether an application is a continuation or continuation-in-part. Stephen G Kunin, Benefit of Prior-Filed Application, USPTO Official Gazette Mar. 18, 2003, available at http://www.uspto.gov/web/offices/com/sol/og/2003/week11/patbene.htm. The present Applicant Entity (hereinafter "Applicant") has provided above a specific reference to the application(s) from which priority is being claimed as recited by statute. Applicant understands that the statute is unambiguous in its specific reference language and does not require either a serial number or any characterization, such as "continuation" or "continuation-in-part," for claiming priority to U.S. patent applications. Notwithstanding the foregoing, Applicant understands that the USPTO's computer programs have certain data entry requirements, and hence Applicant is designating the present application as a continuation-in-part of its parent applications as set forth above, but expressly points out that such designations are not to be construed in any way as any type of commentary and/or admission as to whether or not the present application contains any new matter in addition to the matter of its parent application(s).

All subject matter of the Related Applications and of any and all parent, grandparent, great-grandparent, etc. applications of the Related Applications is incorporated herein by reference to the extent such subject matter is not inconsistent herewith.

BACKGROUND

The description herein generally relates to the field of ultra-high temperature (UHT) pasteurization. Pasteurization and UHT pasteurization has been used to at least partially sterilize milk and other food products. However, conventional pasteurization and conventional UHT pasteurization has been limited to applications in which substantial power is readily available for the pasteurizing process.

There is a need for advantageous structures and methods for performing UHT pasteurization which consumes substantially less power than conventional techniques by the use of microchannels and the like in a variety of structures and in a variety of usage.

SUMMARY

In one aspect, a method of sterilizing a liquid food product includes flowing a food product to be sterilized through an input channel. The method also includes flowing the liquid food product through a heating channel that is fluidly coupled to the input channel. Further, the method includes flowing the food product through an output channel fluidly coupled to the heating channel. The output channel is adjacent the input channel, and the output channel, the input channel, and the heating channel are all integrated portions of a heat exchanger. Further still, the method includes transferring heat between the output channel and the input channel.

In addition to the foregoing, other method aspects are described in the claims, drawings, and text forming a part of the present disclosure.

In one or more various aspects, various structural elements may be employed depending on design choices of the system designer.

In one aspect, a method of heating a food product includes flowing a liquid food product through an input channel. The method also includes flowing the liquid through a heating channel that is fluidly coupled to the input channel. The liquid is transiently heated to a predetermined temperature. Further, the method includes flowing the liquid through an output channel fluidly coupled to the heating channel. The output channel is adjacent the input channel, and the output channel, the input channel, and the heating channel are all integrated portions of a heat exchanger. Still further, the method includes transferring heat between the output channel and the input channel.

In another aspect, a method of sterilizing a liquid includes flowing a liquid through an input channel. The method includes flowing the liquid through a heating channel that is fluidly coupled to the input channel. The liquid is transiently heated to a predetermined temperature. Further, the method includes flowing the liquid through an output channel fluidly coupled to the heating channel. The output channel is adjacent the input channel, and the output channel, the input channel, and the heating channel are all integrated portions of a heat exchanger. Further still, the method includes transferring heat between the output channel and the input channel.

In yet another aspect, a method of heating a liquid includes flowing a liquid to be heated through an input channel. The method also includes receiving heat by the flowing liquid. The heat is received from an output channel. Further, the method includes flowing the liquid through a heating channel that is fluidly coupled to the input channel. The liquid is heated to a predetermined temperature for at least a predetermined time. Further sill, the method includes flowing the liquid through an output channel fluidly coupled to the heating channel. The output channel is adjacent the input channel. The input channel and the output channel are microchannels.

In still yet another aspect, a method of heating a fluid includes flowing a liquid to be heated through an input channel. The method also includes receiving heat by the flowing liquid. The heat is received from an output channel. The method further includes flowing the liquid through a heating channel that is fluidly coupled to the input channel. The liquid is heated to a predetermined temperature for at least a predetermined time. Yet further still, the method includes flowing the liquid through an output channel fluidly coupled to the heating channel. The output channel is adjacent the input channel. The input channel and the output channel are configured such that the flow of the liquid has substantially laminar flow.

In addition to the foregoing, other system aspects are described in the claims, drawings, and text forming a part of the present disclosure.

In addition to the foregoing, various other method and/or system and/or program product aspects are set forth and described in the teachings such as text (e.g., claims and/or detailed description) and/or drawings of the present disclosure.

The foregoing is a summary and thus contains, by necessity, simplifications, generalizations and omissions of detail; consequently, those skilled in the art will appreciate that the summary is illustrative only and is NOT intended to be in any way limiting. Other aspects, features, and advantages of the devices and/or processes and/or other subject matter described herein will become apparent in the teachings set forth herein.

BRIEF DESCRIPTION OF THE FIGURES

The foregoing summary is illustrative only and is not intended to be in any way limiting. In addition to the illustrative aspects, embodiments, and features described above, further aspects, embodiments, and features will become apparent by reference to the drawings and the following detailed description, of which:

FIG. 12 is an exemplary depiction of an alternative counterflow heat exchanger.

DETAILED DESCRIPTION

Figure 1:
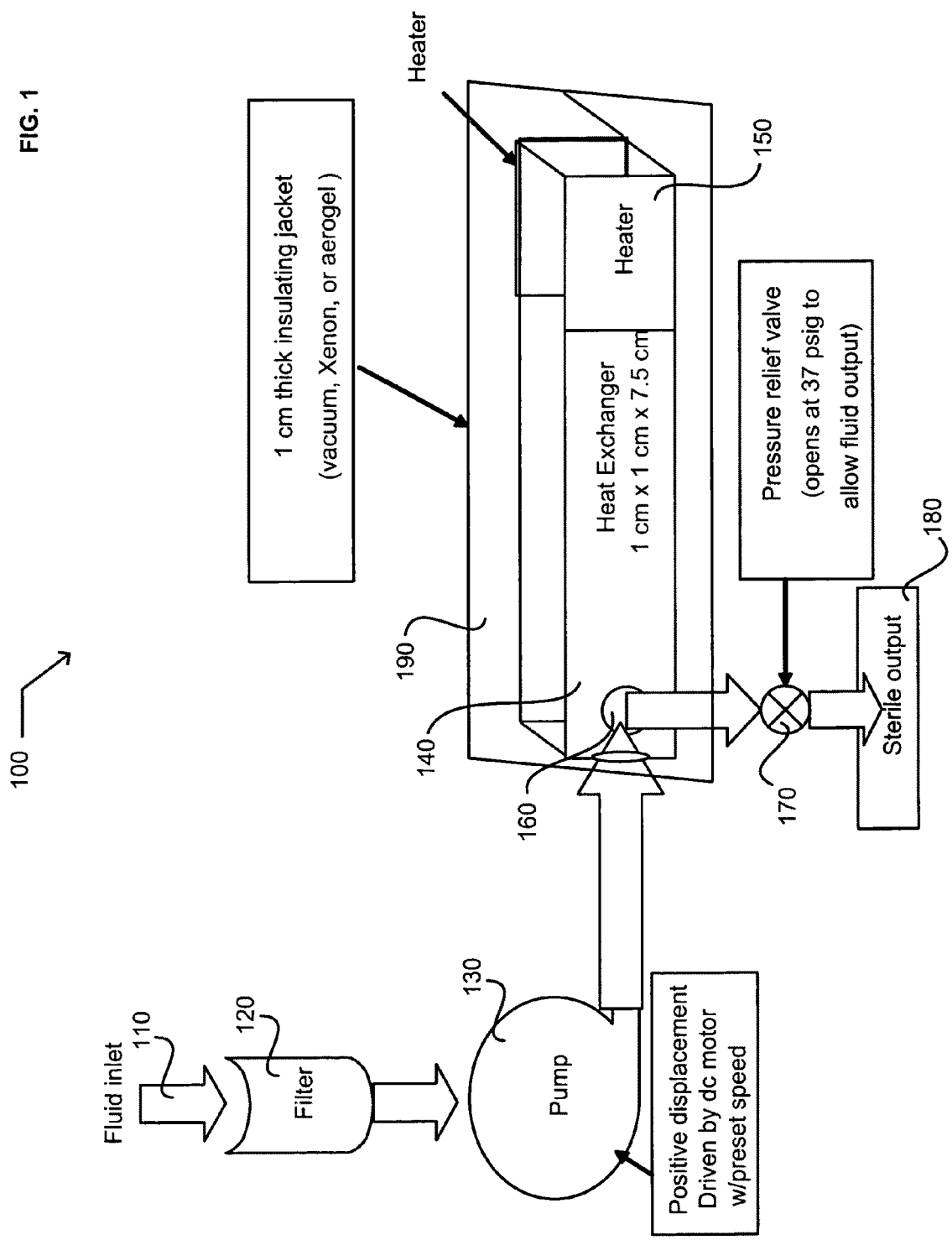
FIG. 1 is an exemplary depiction of a food product sterilization system.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. Those having skill in the art will recognize that the state of the art has progressed to the point where there is little distinction left between hardware and software implementations of aspects of systems; for example the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and or firmware.

Pasteurization is a process that is conventionally used to slow microbial growth in food. Pasteurization is a type of sterilization process that is generally not intended to kill all pathogenic micro-organisms in the food or liquid. Instead, pasteurization aims to reduce the number of viable pathogens so they are unlikely to cause disease (assuming the pasteurization product is refrigerated and consumed before its expiration date). However, although much focus of the description may be on pasteurization processes and more particularly on ultra-high temperature pasteurization processes, the subject matter herein disclosed may be applied both to pasteurization as well as other sterilization processes, whether they be complete or incomplete.

Pasteurization conventionally uses temperatures below boiling temperatures since at temperatures above the boiling point for milk, e.g., casein micelles will irreversibly aggregate (or "curdle"). There are three main types of pasteurization used today: High Temperature/Short Time (HTST), Extended Shelf Life (ESL) treatment, and ultra-high temperature (UHT or ultra-heat treated) is also used for milk treatment. In the HTST process, milk is forced between metal plates or through pipes heated on the outside by hot water, and is heated to 71.7° C. (161° F.) for 15-20 seconds. UHT processing holds the milk at a temperature of approximately 135° C. (275° F.) for a time period ranging from a fraction of a second to a couple of seconds; this temperature is above the boiling point of milk at normal atmospheric pressures, but boiling can be suppressed by operating at a pressure substantially above atmospheric pressure. The use of a short exposure time minimizes the detrimental effects on taste and protein constituents that would normally occur at 135° C. ESL milk has a microbial filtration step and lower temperatures than HTST.

There exist many food products that may be pasteurized. These food products include but are not limited to beer, cider, fruit juice, maple syrup, milk, wine, soy sauce, sports drinks, water, etc.

In regions including Africa and South Asian countries, it is common to boil milk to sterilize it after it is harvested. This intense heating greatly changes the flavor of milk and may require a substantial amount of energy, which may be limited. Some of the diseases that boiling of or pasteurization may prevent include but are not limited to tuberculosis, diphtheria, salmonellosis, strep throat, scarlet fever, listeriosis and typhoid fever.

UHT pasteurization is the partial sterilization of food by heating it for a short time, around 1-2 seconds, at a temperature exceeding 135° C. (275° F.), which is the temperature required to kill spores some spores which may be found in milk. The most common UHT product is milk, but the process is also used for fruit juices, cream, yogurt, wine, soups, and stews, etc.

Advantageously, UHT milk has a typical shelf life of six to nine months, until opened, which is higher than provided by traditional lower-temperature pasteurization processes.

Referring now to FIG. 1, an exemplary system 100 for pasteurizing (or alternatively sterilizing) milk or other food products or liquids, is depicted. Such liquids may include but are not limited colloids and suspensions, etc. System 100 includes a fluid inlet 110 for introducing the food product or other liquid. A filter 120 receives the fluid and filters any particulate or other solids from the fluid. Filter 120 feeds into a pump 130 that pressurizes the fluid in system 100. Pump 130 may be, but is not limited to, a positive displacement pump that is run by a DC motor with a preset or controllable speed. Pump 130 feeds the fluid into a heat exchanger 140. In accordance with an exemplary embodiment heat exchanger 140 may be a microchannel heat exchanger having fluid channels with a high aspect ratio, small hydraulic diameter, and other characteristics similar to other microchannel devices such as but not limited to microchannel coolers for cooling integrated circuits, solid-state lasers, and the like. Heat exchanger 140 includes a heater 150 which heats a portion of heat exchanger 140 and the fluid flowing therethrough such that the fluid reaches the UHT pasteurization temperature or other predetermined temperature for a predetermined time, such as but not limited to 1-2 seconds. Heat exchanger 140 includes a heat exchanger outlet 160 that feeds into a pressure relief valve 170, which in an exemplary embodiment will not open unless the pressure reaches a predetermined pressure, such as but not limited to 37 psi. Such fluid is released through a sterile output 180 into sterile receptacles or packages. Heat exchanger 140 may be at least partially encased by an insulating layer 190 which may be but is not limited to a vacuum jacket, or a chamber of Xenon gas, or an aerogel foam, or other insulating material.

Microchannels have been proposed to cool integrated circuits and have been understood since the early 1980s and disclosed in research published by Dr. David Tuckerman and Prof. R. Fabian Pease. Tuckerman and Pease published research showing that microchannels etched into silicon may provide densities as high as 1000 W per square centimeter. Such microchannel structures have been shown to be capable of cooling integrated circuits, such as described in U.S. Pat. Nos. 4,541,040; 7,156,159; 7,185,697; and U.S. Patent Application Publication No. 2006/0231233 all of which are herein incorporated by reference. However, practical application to pasteurization, sterilization, or transient heating of a fluid flow has not been accomplished or suggested.

One of the advantages of using the microchannel structures is that turbulent flow within the channels is not necessary to increase heat transfer efficiency. Microchannel structures neither require nor create turbulent flow. Conventional macro-channels require turbulence to increase heat transfer rate, otherwise the fluid acts as an insulator between the channel wall and the center of the fluid flow, which is known as a thermal boundary layer. Turbulent flow within the fluid channel mixes the fluid next to the wall of the channel with the fluid in the middle of the channel, thereby minimizing the thickness of the thermal boundary layer and maximizing the rate of heat transfer between the fluid and the wall. However, such turbulence and mixing requires high flow velocities and high pressures. In addition, the high flow velocities would require that the heat exchanger channels be very long in order to achieve the 2-second residence time at 135° C. recommended for UHT sterilization. Microchannels, instead, have the advantage that the heat transfer coefficient "h" is inversely proportional to the width of the channel. As "h" increases, efficiency increases. A very narrow channel has a thin thermal boundary layer, because the boundary layer cannot be larger than ½ the channel width. Thus, heat is transferred between the wall and the center of the channel with very little thermal resistance. Accordingly, it may be beneficial to use a microchannel or microchannel-like heat exchanger for UHT pasteurization in order to increase heat transfer and therefore enable a very compact design that requires a relatively low energy input.

Figure 2:
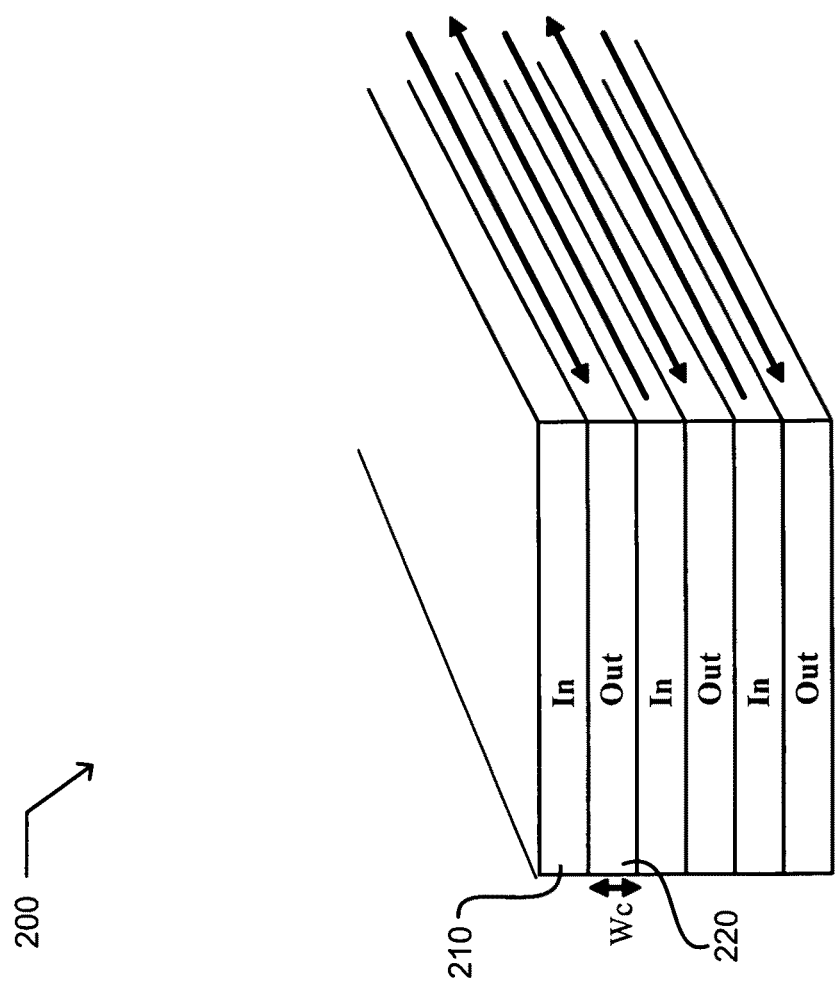
FIG. 2 is an exemplary depiction of a counterflow heat exchanger.

Referring now to FIG. 2, an exemplary perspective cross-section of a counterflow heat exchanger 200, which may be used as heat exchanger 140 of FIG. 1. Heat exchanger 200 includes a stack of flow channels. Stack of flow channels includes a repeated series of inflow channels 210 alternating with outflow channels 220. In such a counterflow heat exchanger, the fluid preferably makes a roundtrip in channel 210 and out of an adjacent channel 220, i.e., the heat exchanger is single-ended with its inputs and outputs at or near the same end. In an advantageous design, excellent heat transfer between channels 210 and 220 is desired while axial heat transfer along the length of the channels is not desired.

Figure 3:
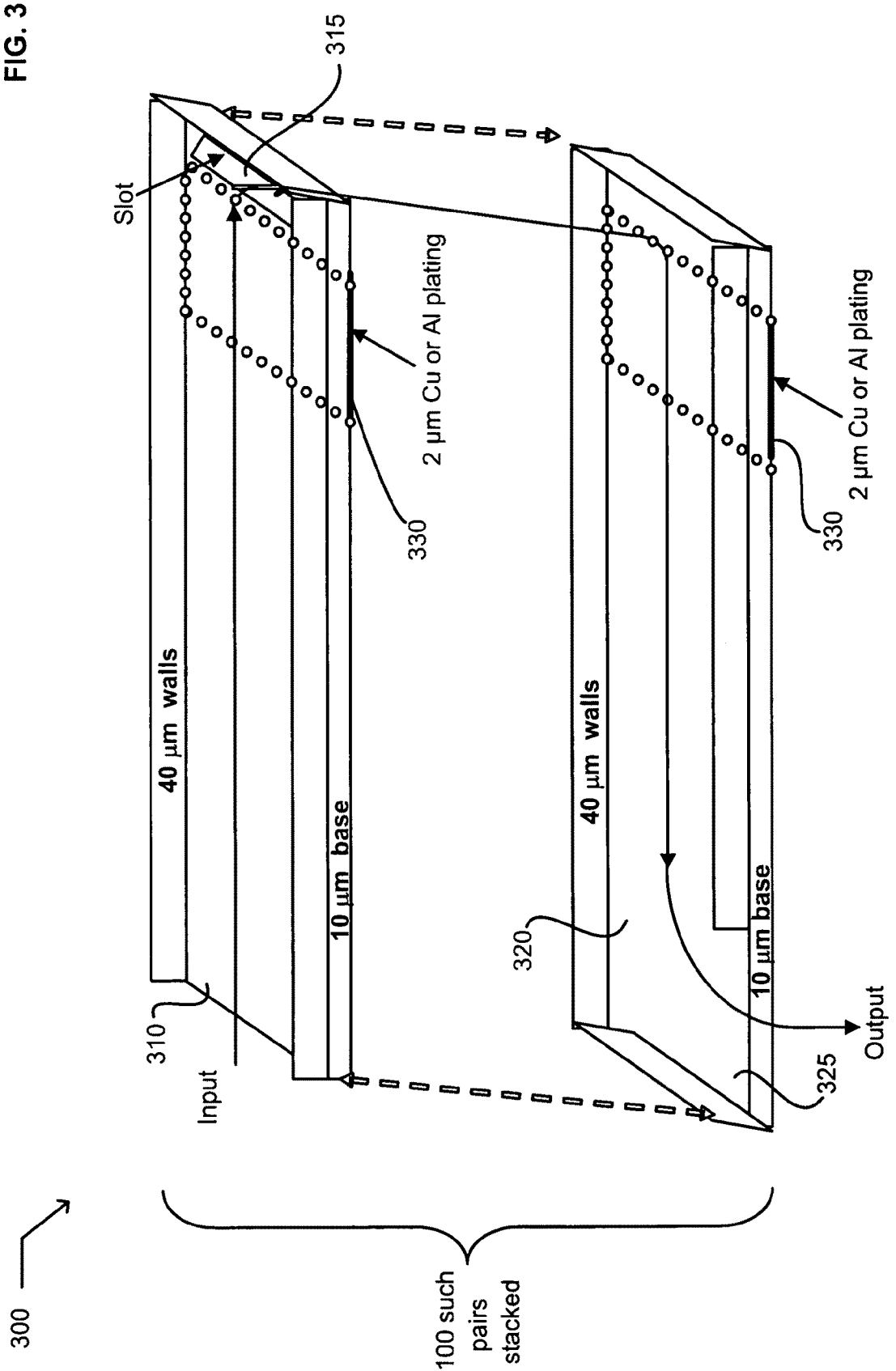
FIG. 3 is an exemplary depiction of an exploded view of a heat exchanger channel pair.

Referring now to FIG. 3, an exemplary exploded view of a channel pair 300 from a counterflow heat exchanger such as but not limited to heat exchanger 200 is depicted. Channel pair 300 includes an inflow channel 310 that includes a slot 315 that fluidly couples channel 310 to channel 320. Channel 320 includes an outlet 325. In an exemplary embodiment, the channels may include thermally conductive plating 330 such as but not limited to Copper or Aluminum plating on a portion of the channels for conducting or applying a heat input to the fluid flow in the channels and maintaining an approximately uniform high temperature over a substantial length of the heat exchanger. In accordance with an exemplary embodiment, the side walls may be on the order of 40-50 microns thick and the base may be on the order of 10-12 microns thick, however the heat exchanger is not limited to these dimensions. In an exemplary embodiment, the heat exchanger may include, but is not limited to, approximately 100 or more of these pairs in stacked relation. In accordance with one exemplary embodiment, the channels may be formed of polyaryletheretherketone (PEEK).

Figure 4:
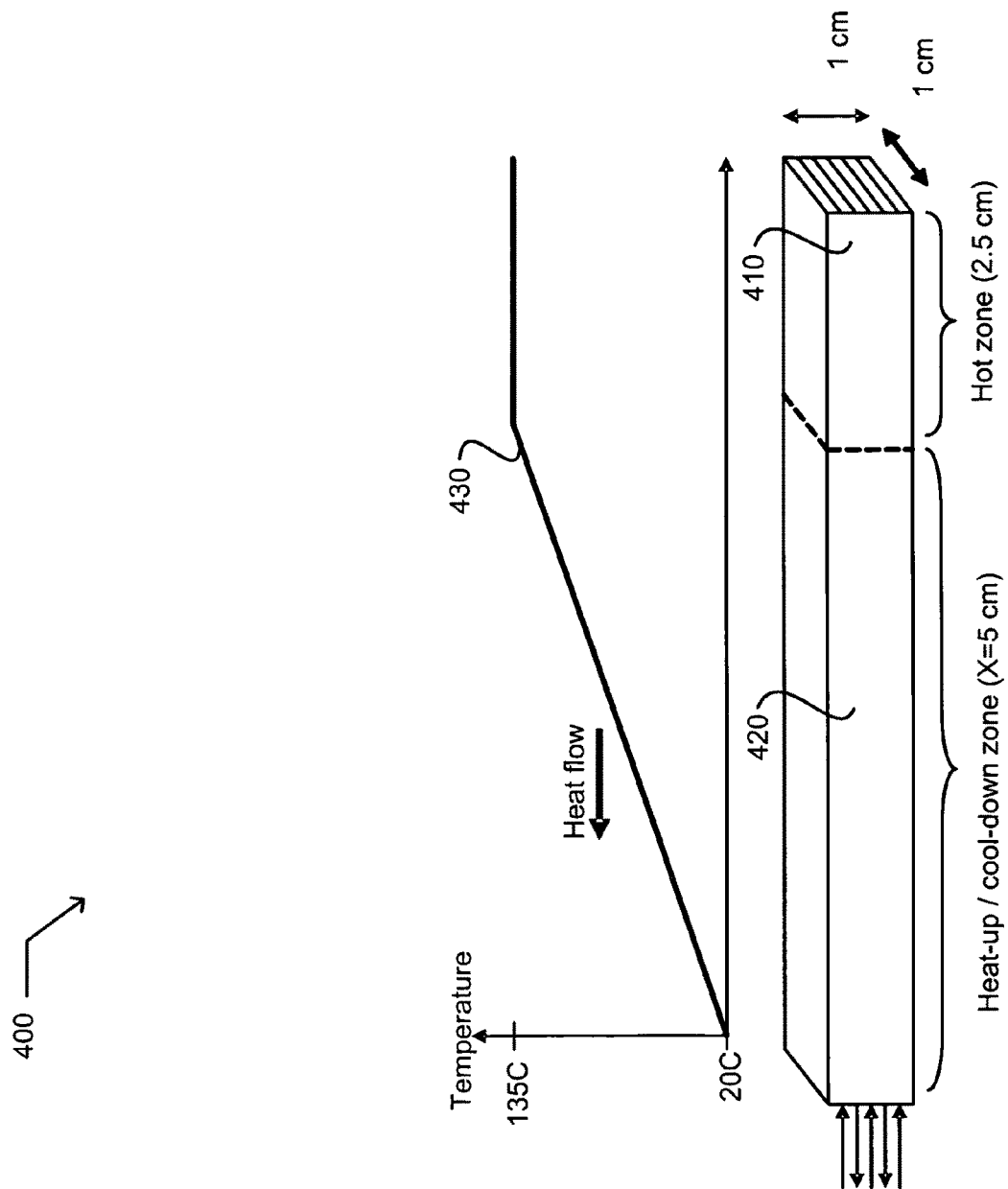
FIG. 4 is an exemplary depiction of a heat exchanger showing axial heat leakage.

Referring now to FIG. 4, a further exemplary depiction of the aforementioned counterflow heat exchanger is depicted. Heat exchanger 400 includes a hot zone 410 in which heat input is applied and a heat-up (for inflows)/cool down (for outflows) zone 420 where much of the heat exchange occurs. An exemplary graph 430 depicts the approximate temperature profile of the fluid flows along the length of the heat exchanger.

Figure 5:
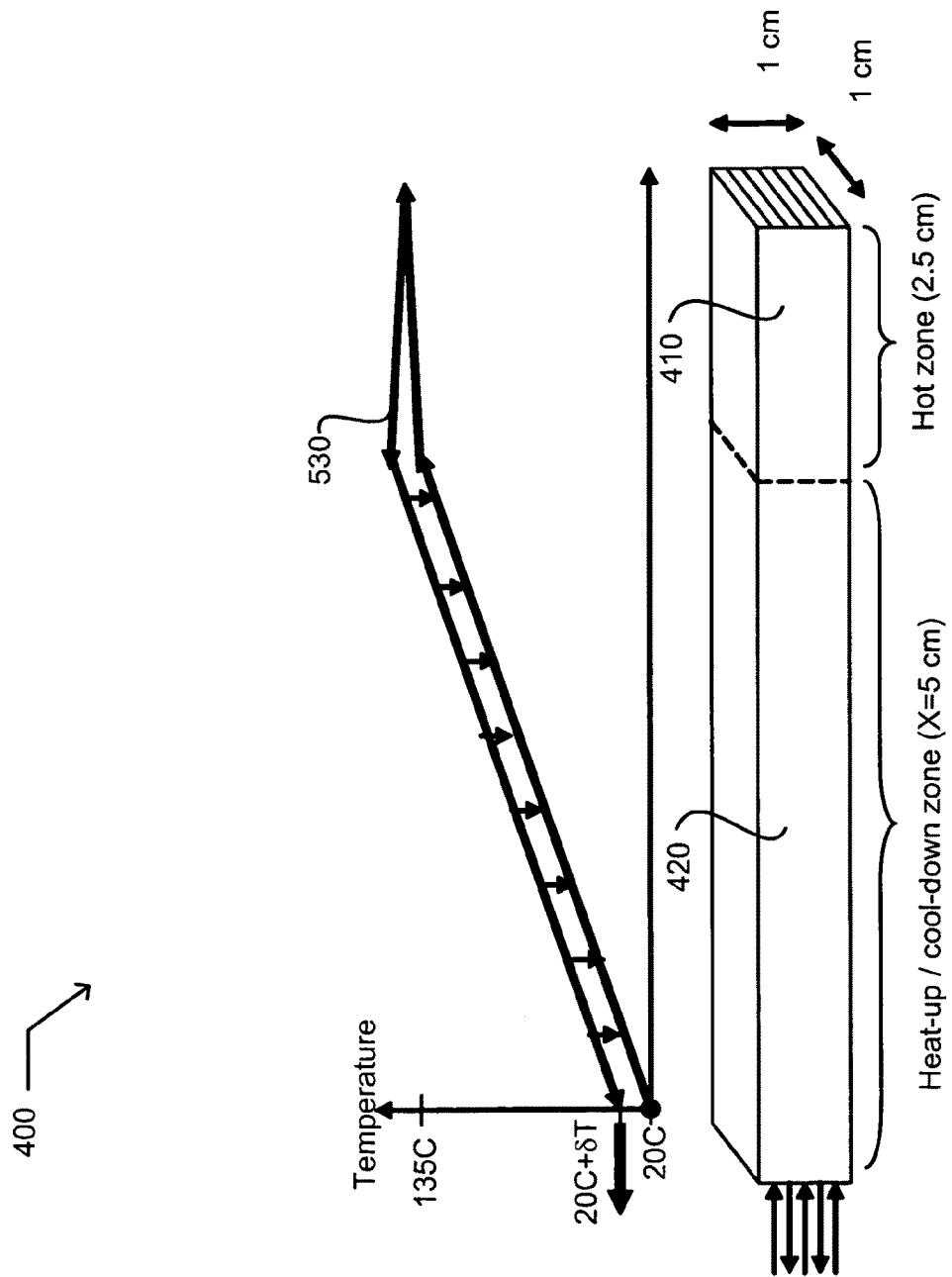
FIG. 5 is an exemplary depiction of a heat exchanger showing temperature profiles and heat flow between adjacent channels.
Figure 6:
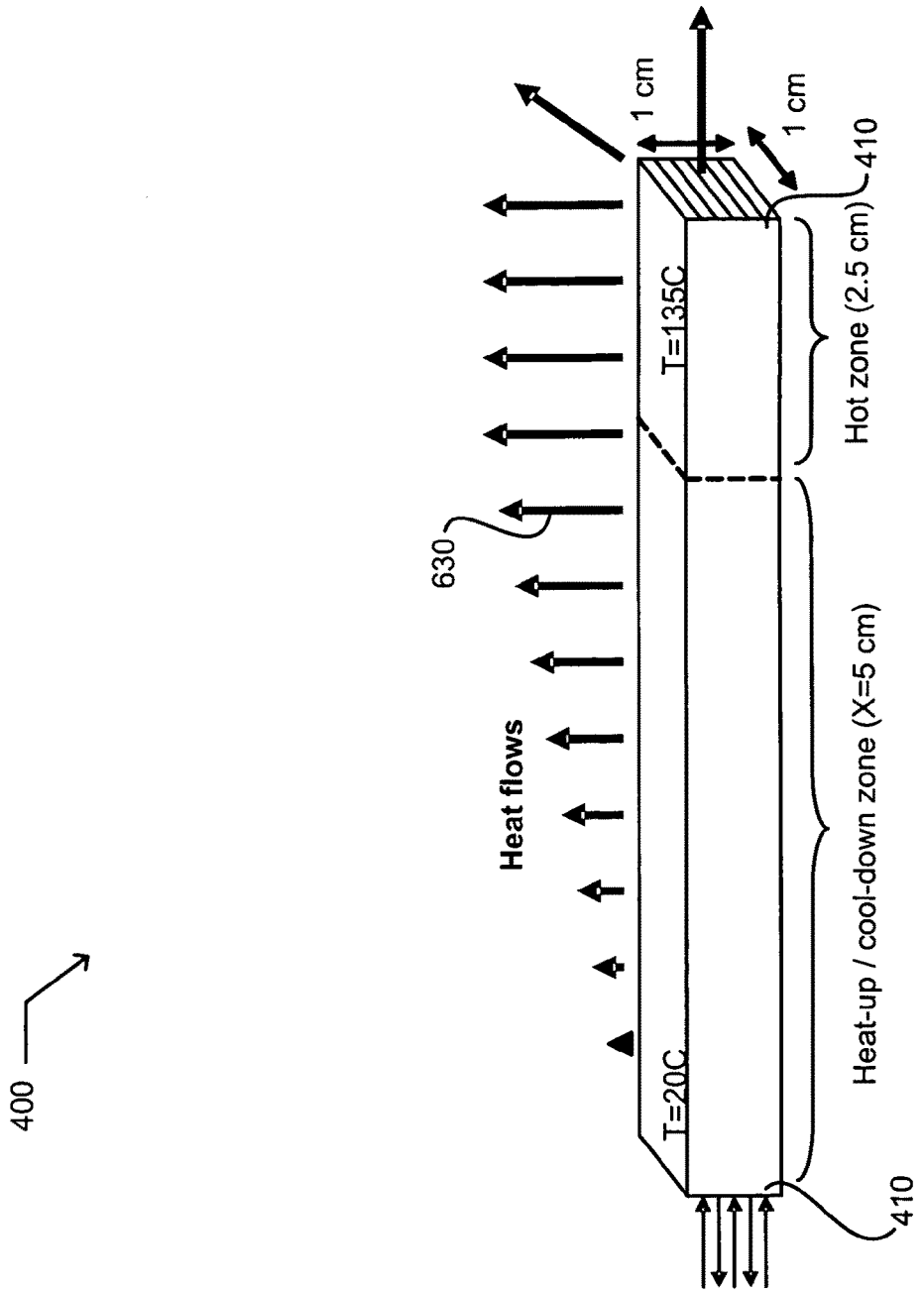
FIG. 6 is an exemplary depiction of a heat exchanger showing radial heat leakage.
Figure 7:
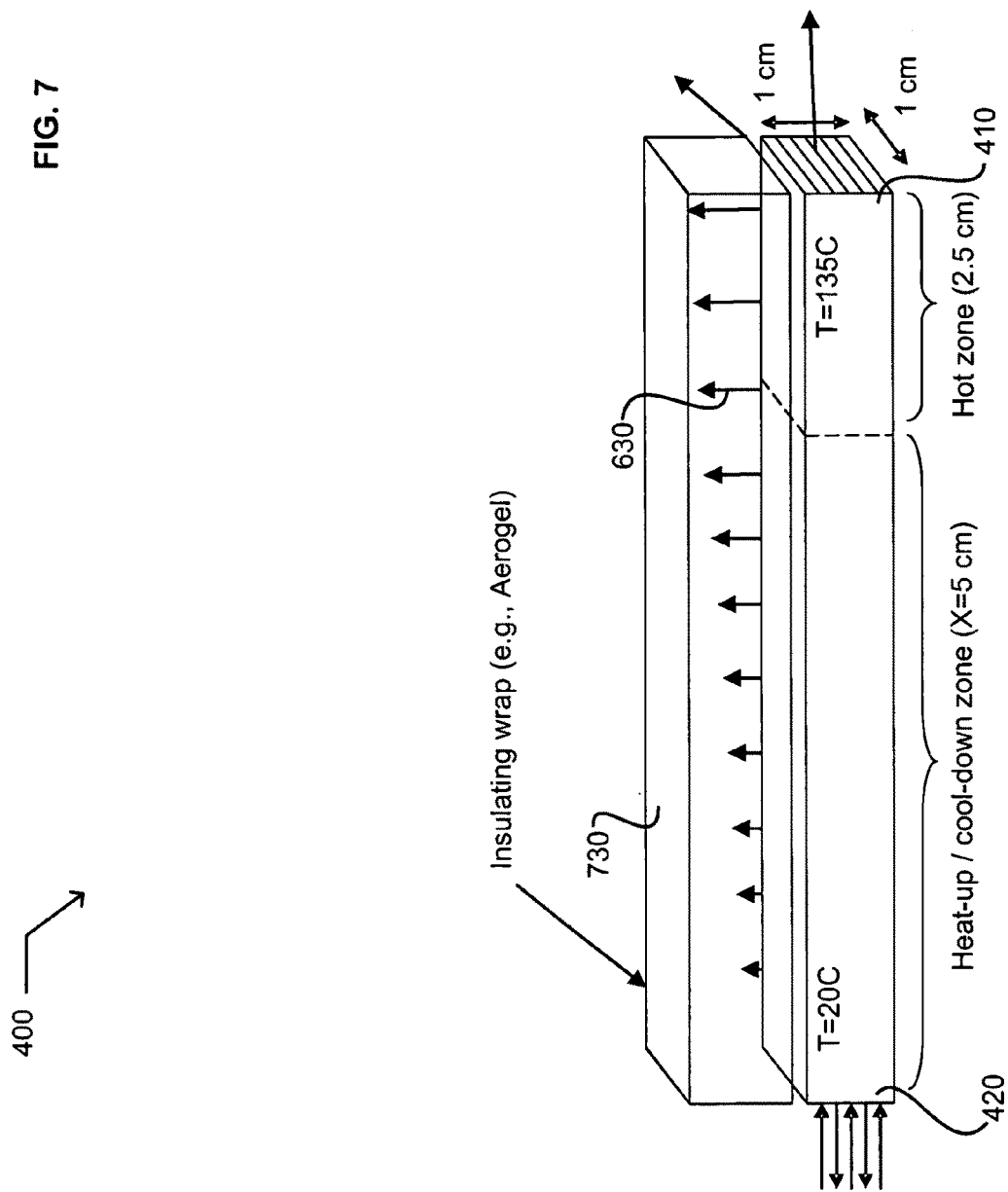
FIG. 7 is an exemplary depiction of a heat exchanger showing heat leakage through an insulating wrap.

With reference to FIG. 5, a depiction of the residual heat in the exiting fluid is provided in graph 530. Such an exemplary depiction illustrates the temperature profiles of both the input and output fluid flow, with the heat exchanger thermodynamic irreversibility illustrated by the temperature increase ST in the exit fluid temperature relatively to the inlet fluid temperature. Said thermodynamic irreversibility represents the minimum thermal energy that must be supplied to the heat exchanger (e.g., to the hot zone) in order to maintain the desired hot zone temperature. Additional energy will be required to overcome parasitic heat leaks such as the axial heat leak illustrated by the arrow labeled 'heat flow' in FIG. 4. An additional heat leak in the radial directions (i.e., outward heat flows in the plane perpendicular to the direction of flow) are illustrated by the arrows 630 in FIG. 6 emanating from heat exchanger 400. FIG. 7 depicts the use of an insulative wrap 730 which may be formed of a variety of materials including but not limited to aerogel, silica aerogel, or Xenon gas, among many other insulation materials. The magnitude of radial heat flows 630 will be reduced in comparison with those in FIG. 6 by virtue of the thermal insulation layer, thereby reducing the thermal energy input required to maintain the hot zone temperature.

Figure 8:
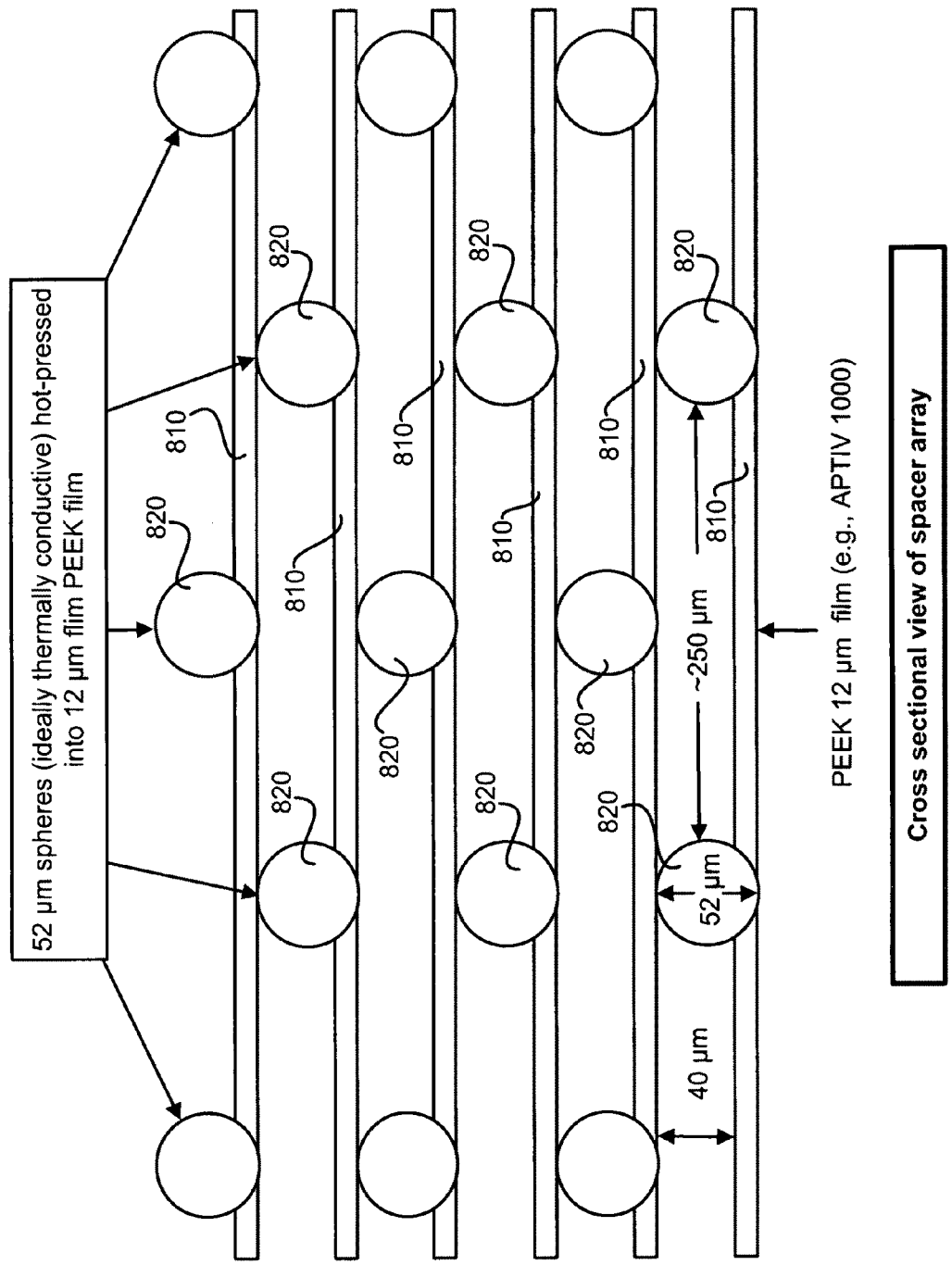
FIG. 8 is an exemplary depiction of heat exchanger channel spacers.

In accordance with an exemplary embodiment, as depicted in FIG. 8, it may be desirable to use 10 or 12 micron PEEK film to construct the channel walls 810 of the heat exchanger. Other thicknesses or other materials with relatively poor thermal conductivity, such as stainless steel, may be equally applicable depending on the desired characteristics. Each of the channel walls may be spaced apart and kept spaced apart by a plurality of spacers 820 which aid in maintaining the channel height in opposition to the pressure differentials between inlet and outlet channels which will exist during operation of the pasteurizer. These spacers 820 may be in the form of ribs or spheres (as depicted) which are pressed onto the film 810 or otherwise attached or formed. Such spacers may preferably be thermally conductive in nature to aid in the heat transfer in the transverse direction, but preferably are non-contiguous in the flow (axial) direction so as to minimize the heat transfer in the axial direction along the length of the heat exchanger. In one preferred embodiment, the spacers in each layer are offset in horizontal location from those in the two immediate adjacent layers. In another embodiment, the spacers are configured in a denser pattern near the input/output ends of the heat exchanger, where the pressure differential between adjacent channels is high, and configured in a sparser pattern near the hot zone, where the pressure differential between input and output channels is low.

Figure 9:
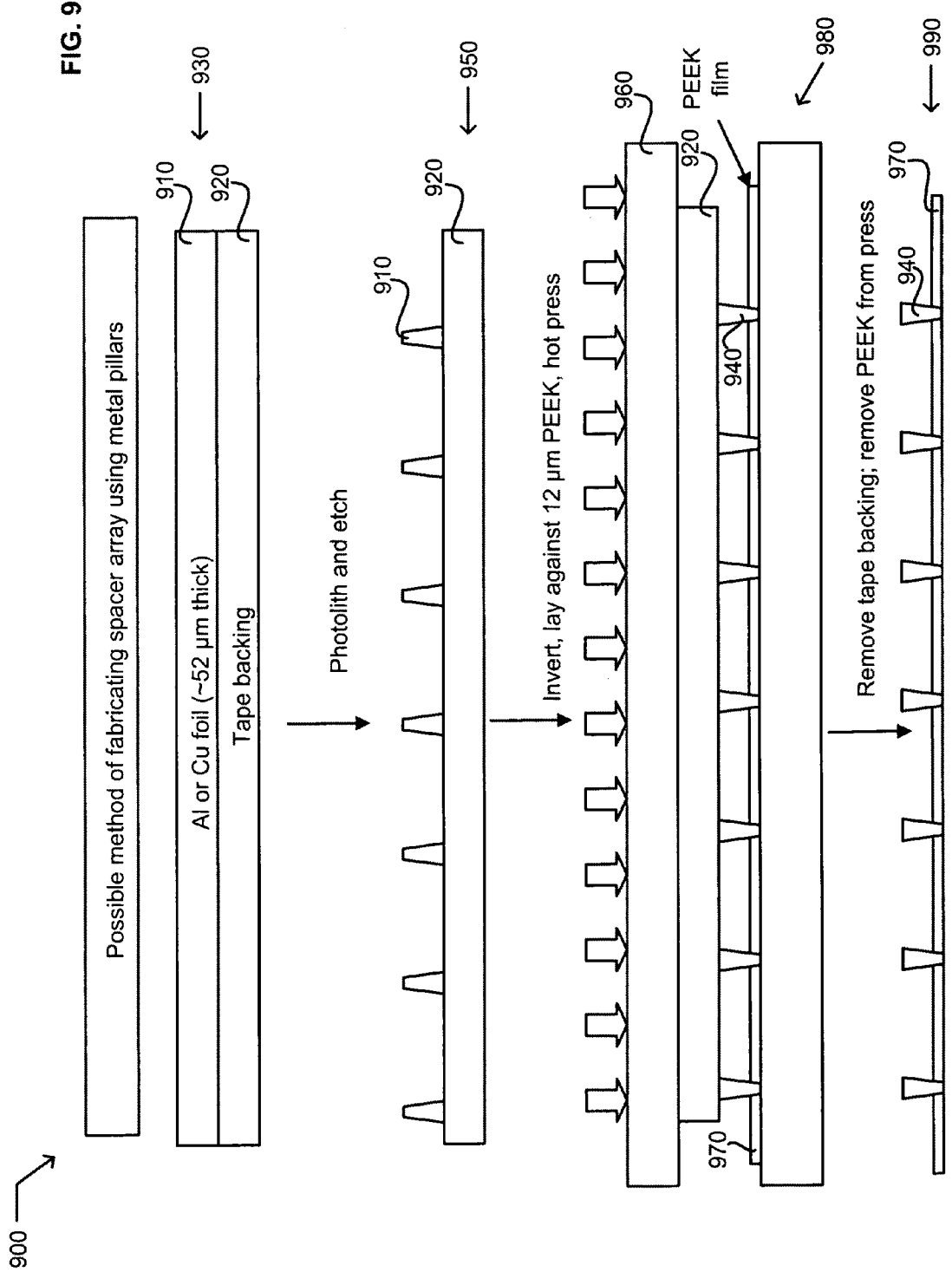
FIG. 9 is an exemplary depiction of a method of forming heat exchanger channel spacers.

Referring now to FIG. 9, a method 900 of fabricating heat exchanger channels is depicted. In the exemplary embodiment, an aluminum or copper foil (on the order of 52 microns thick) 910 is adhered to a tape backing 920 (process 930). Using photolithography and etching techniques material is removed leaving behind aluminum or copper posts 940 adhered to the tape backing 920 (process 950). The copper posts 940 and tape backing 950 are inverted and placed between plates 960 of a hot press. The posts 940 are pressed into a sheet of PEEK 970 (process 980). The hot press plates 960 and the tape backing 920 are removed leaving behind a sheet of PEEK 970 with posts 940 to provide spacing and support for a heat exchanger to be assembled from stacked layers of these (process 990).

Figure 10:
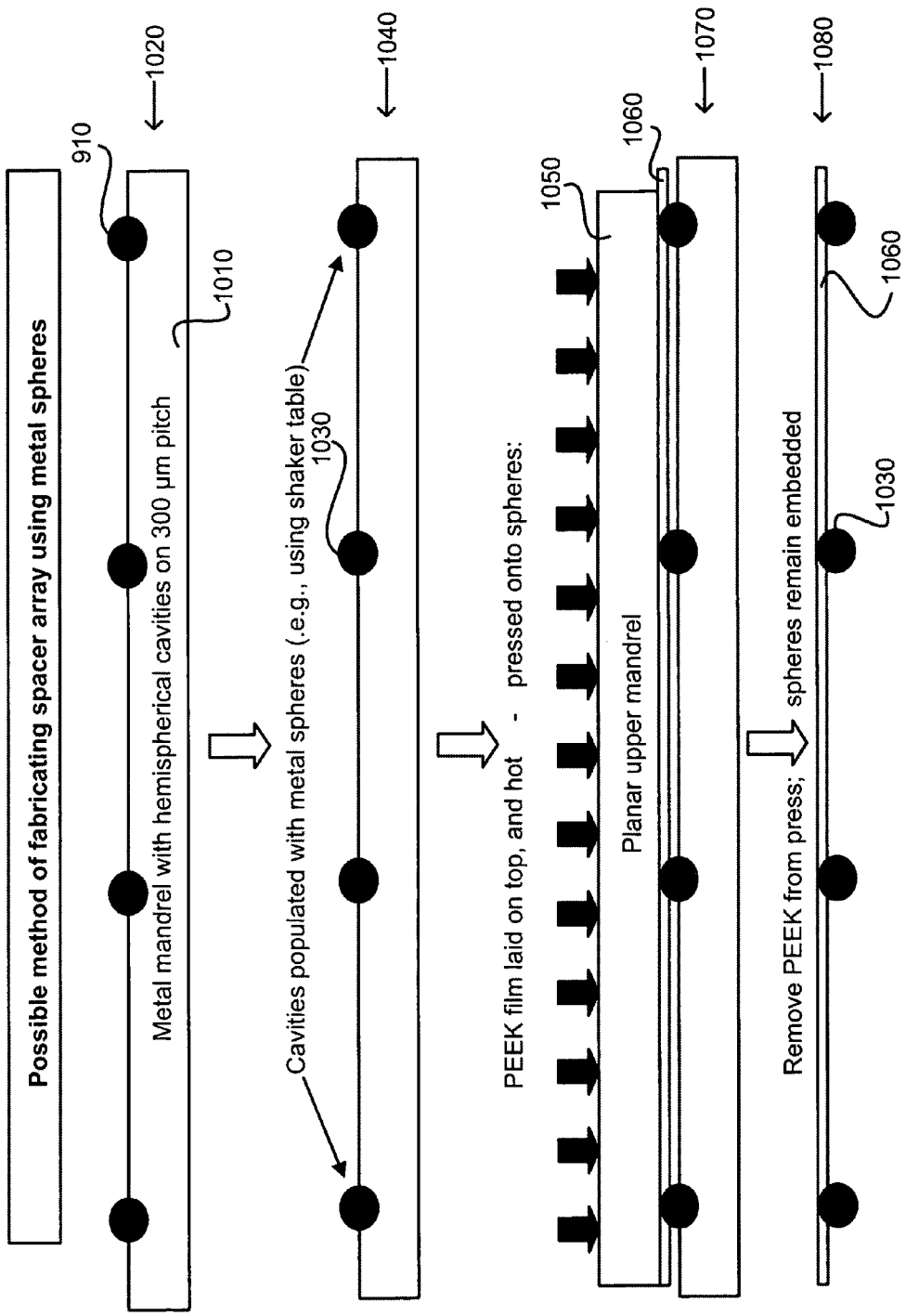
FIG. 10 is an exemplary depiction of a method of forming heat exchanger channel spacers.

Referring now to FIG. 10, an alternative method 1000 of forming a spacer array to be fabricated using a 300 micron metal sheet 1010 having depressions 1015 is depicted (process 1020). The depressions or cavities 1015 are populated with metal spheres 1030 using a shaker table or other methods (process 1040). PEEK film 1060 is overlaid on the metal spheres 1030 and hot pressed using an upper mandrel 1050 (process 1070). The PEEK is removed from the press and the spheres remain embedded in the PEEK (process 1080) to be formed into the heat exchanger.

Figure 11:
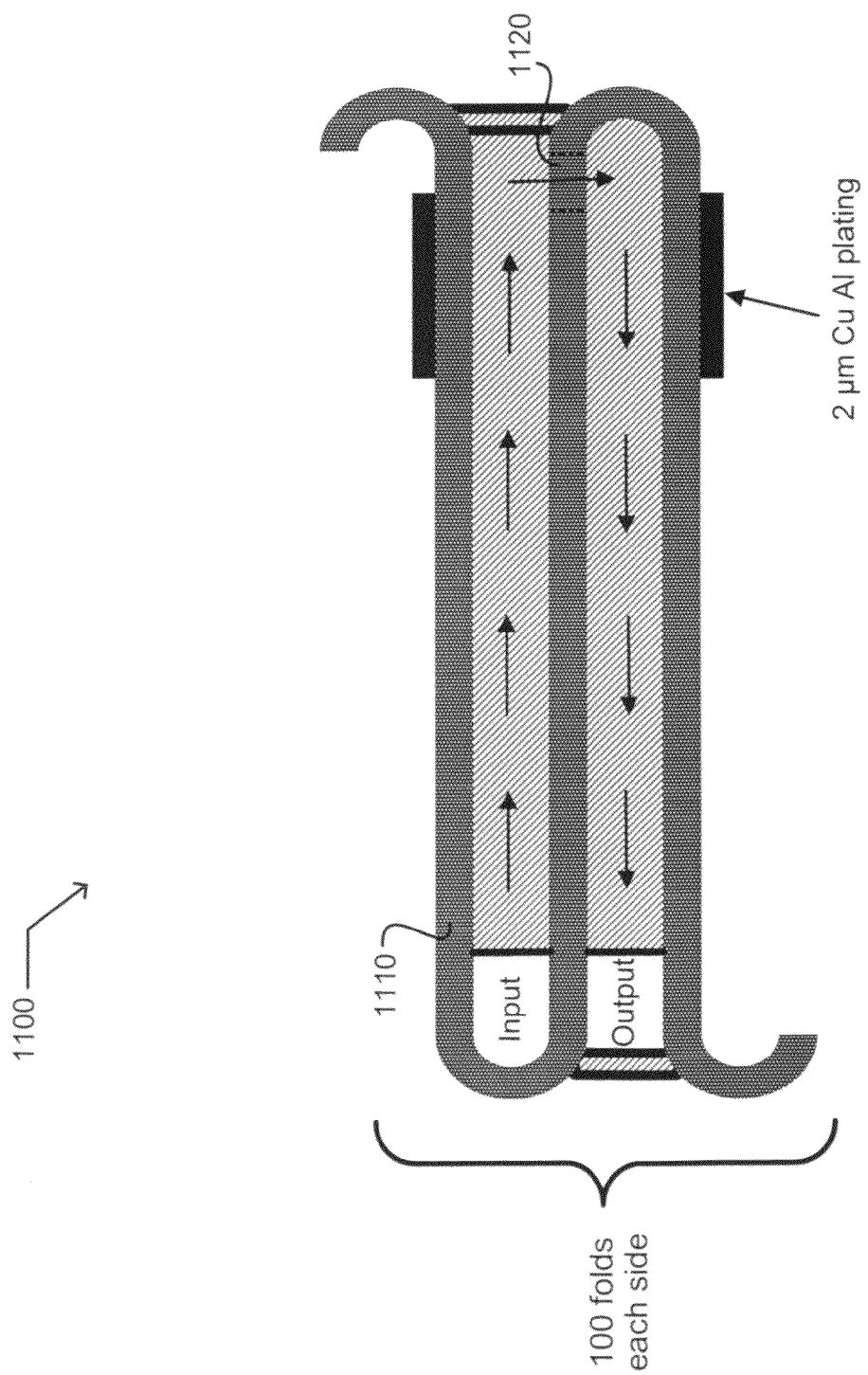
FIG. 11 is an exemplary depiction of an alternative counterflow heat exchanger.

In yet another exemplary embodiment, an alternative manufacturing technique 1100 is depicted in FIG. 11 which does not require the handling of 100 or more individual piece parts. A first channel and a second channel running adjacent one another are formed from a single strip or ribbon of PEEK material 1110 by folding over the material on itself to form a stack of channels pairs of which are linked by slots 1120. Other concepts for manufacturing the heat exchanger and materials that are applicable may also be used.

Referring now to FIG. 12, a double-ended pass through heat exchanger 1200 is depicted. Pass through heat exchanger 1200 includes channels 1210 having flow in one direction through a heater 1230. Flow through channel 1210 receives heat input from flow 1220 in the opposite direction before entering heater 1230. Flow through channel 1210 provides heat to flow 1220 after flowing through heater 1230. In the exemplary embodiment, the fluid flows through channels 1210 and 1220 simultaneously in an interleaved configuration, and does not make a roundtrip as in the exemplary embodiments described above. This pass through heat exchanger therefore may have the advantage in eliminating turns in the fluid flow channel. In a preferred embodiment, the mass flow rates going in one direction are closely controlled so as to be equal and opposite to the mass flow rates going in the opposite direction.

In one exemplary embodiment, the input and output channels are separated by a thin wall having a thickness in the range of about 0.01 centimeters to 0.001 centimeters. Although these thicknesses may be desirable, other thicknesses may be used. With the heat exchanger provided above, it may be desirable to construct it in such a manner that at least 90% of the heat input is provided by a heater that is thermally coupled to the hot zone. In one exemplary embodiment the input channel and the output channels each have a hydraulic diameter that is less than approximately one millimeter, where the hydraulic diameter is four times the cross sectional area of the channel divided by the perimeter of the cross section. In one exemplary embodiment a highly conductive material is disposed between the heater and the channel. In accordance with an exemplary embodiment, the highly conductive material may be copper, other metals or metal alloys or other highly conductive materials. In accordance with an exemplary embodiment, a sensor may be used to sense at least one characteristic of the food product. The sensor may be but is not limited to a temperature transducer, a pressure transducer, a flow transducer, etc.

The use of a sensor allows for the closed loop controllability of the sterilizer system. In an exemplary embodiment computer or microprocessor controllers may be implemented to control temperature, heater, pump, fluid flow, valves, etc. Such a controller may use any of a variety of algorithms and employ any type of applicable hardware and software components.

In accordance with an exemplary embodiment, the heating structure in the heat exchanger includes a heating element with highly conductive materials to transfer the heat to the fluid channels. Alternatively, active heating structures may be coupled directly to the microchannels instead of using the highly conductive materials to transfer the heat.

In many of the exemplary embodiments disclosed, it has been contemplated to use the heat exchanger for sterilization of food products. However, the heat exchanger structure may also be used in other applications including but not limited to various types of brewing applications, making yogurt, fermentation processes, sustaining or participating in a chemical or biological reaction, etc. Further, in an exemplary embodiment the heat exchanger may be used in polymerase chain reaction (PCR) processes for the rapid duplication of DNA.

The heat exchanger described above is contemplated to increase efficiency during a transient heating process. In accordance with an exemplary embodiment the heat exchanger may be designed to heat milk or water to a temperature of approximately 135 degrees C. and hold it at that temperature for approximately 2 seconds and then cool down the fluid while recovering the vast majority of the heat such that energy input is minimal compared with conventional UHT pasteurization processes. In accordance with an exemplary embodiment it is advantageous to maintain axial heat flow (along the flow path) to a minimum while maximizing heat transfer between the channels in an attempt to maximize efficiencies of the heat exchanger.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. Further, those skilled in the art will recognize that the mechanical structures disclosed are exemplary structures and many other forms and materials may be employed in constructing such structures.

In a general sense, those skilled in the art will recognize that the various embodiments described herein can be implemented, individually and/or collectively, by various types of electro-mechanical systems having a wide range of electrical components such as hardware, software, firmware, or virtually any combination thereof; and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electro-mechanical systems include but are not limited to a variety of consumer electronics systems, as well as other systems such as motorized transport systems, factory automation systems, security systems, and communication/computing systems. Those skilled in the art will recognize that electro-mechanical as used herein is not necessarily limited to a system that has both electrical and mechanical actuation except as context may dictate otherwise.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation.

One skilled in the art will recognize that the herein described components (e.g., steps), devices, and objects and the discussion accompanying them are used as examples for the sake of conceptual clarity and that various configuration modifications are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific components (e.g., steps), devices, and objects herein should not be taken as indicating that limitation is desired.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

The invention claimed is:

1. A method of sterilizing a liquid food product, comprising:

flowing a liquid food product to be sterilized through an input channel;

flowing the food product through a heating channel that is fluidly coupled to the input channel, the heating channel including an actively heated zone wherein a heater provides thermal energy to the actively heated zone through a direct thermal coupling of the heater to the actively heated zone;

flowing the food product through an output channel fluidly coupled to the heating channel, the output channel being adjacent the input channel, the input channels and the output channels are configured to induce liquid flow in the channel with a Reynolds number of less than 2000 with a boundary layer thickness that is greater than one-half the thickness of the channels, and the output channel, the input channel, and the heating channel all being integrated portions of a heat exchanger; and transferring heat between the output channel and the input channel, the input channel and the output channel each having a plate-like layout in which the width of the channel is at least ten times the thickness of the channel, the thickness of the channel extending between shared walls of the input channel and the output channel and the input channels alternate with the output channels in a side-to-side relationship with support elements within at least some of the input channels and output channels.

2. The method of sterilizing a food product of claim 1, wherein the input channel and the output channel are separated by a thin wall and the thin wall has a thickness less than 0.01 centimeters.

3. The method of sterilizing a food product of claim 1, wherein the input channel and the output channel are separated by a thin wall and the thin wall has a thickness less than 0.002 centimeters.

4. The method of sterilizing a food product of claim 1, wherein the input channel and output channel share a wall and there exist multiple pairs of input channels and output channels in a row each pair sharing a wall with an adjacent pair.

5. The method of sterilizing a food product of claim 1 wherein the input channel and output channel share a wall, the input and output channels being at least partially surrounded by an insulating layer.

6. The method of sterilizing a food product of claim 1, wherein the input and output channels each having a hydraulic diameter, expressed as four times the cross sectional area of the channel divided by the perimeter of the cross section, that is less than approximately one millimeter.

7. The method of sterilizing a food product of claim 1, wherein the input and output channels each having a hydraulic diameter, expressed as four times the cross sectional area of the channel divided by the perimeter of the cross section, that is less than approximately one hundred micrometers.

8. The method of sterilizing a food product of claim 1, wherein the input channel and the output channel are at least partially formed of polyaryletheretherketone (PEEK).

9. The method of sterilizing a food product of claim 1, wherein the food product includes at least one of fruit juice, apple cider, honey, maple syrup, milk, soy sauce, sports drinks, vinegar, water, wine, beer, cream, and cheese.

10. The method of sterilizing a food product of claim 1, further comprising pressurizing the food product.

11. The method of sterilizing a food product of claim 1, further comprising filtering the food product.

12. The method of sterilizing a food product of claim 1, further comprising sensing at least one characteristic of the food product.

13. The method of sterilizing a food product of claim 1, further comprising sensing at least one characteristic of the food product, wherein the sensor is a temperature transducer.

14. The method of sterilizing a food product of claim 1, further comprising sensing at least one characteristic of the food product, wherein the sensor includes a pressure transducer.

15. The method of sterilizing a food product of claim 1, further comprising sensing at least one characteristic of the food product, wherein the sensor includes a flow transducer.

16. The method of sterilizing a food product of claim 1, wherein an output channel is adjacent to and transfers heat to multiple input channels.

17. The method of sterilizing a food product of claim 1, wherein there are multiple input channels and output channels and the input channels and output channels are formed as an array of adjacent tubes.

18. The method of sterilizing a food product of claim 1, wherein there are multiple input channels and output channels and the input channels and output channels are formed as a grid of adjacent channels.

19. The method of sterilizing a food product of claim 1, wherein there are multiple input channels or output channels and at least one set of input channels or output channels are interconnected.

20. The method of sterilizing a food product of claim 1, further comprising a flow reversal section between at least part of the input channel and at least part of the output channel.

21. The method of sterilizing a food product of claim 1, further comprising a flow reversal section between at least part of the inlet channel and at least part of the output channel and the flow reversal section is proximate the heating section.

22. The method of sterilizing a food product of claim 1, wherein the input channel flow is in the opposite direction as the output channel flow.

23. The method of sterilizing a food product of claim 1, wherein the input channel and the output channel have variable lateral cross-sections but the sum of the cross sectional area of adjacent lateral cross sections of the input channel and the output channel is a constant.

24. The method of sterilizing a food product of claim 1, wherein the input channel and the output channel do not include a flow reversal section.

25. A method of heating a liquid food product, comprising:
flowing a liquid food product through an input channel;
flowing the liquid through a heating channel that is fluidly coupled to the input channel, the heating channel including an actively heated zone wherein a heater provides thermal energy to the actively heated zone through a direct thermal coupling of the heater to the actively heated zone, the liquid being transiently heated to a predetermined temperature;
flowing the liquid through an output channel fluidly coupled to the heating channel, the output channel being adjacent the input channel, the input channels and the output channels are configured to induce liquid flow in the channel with a Reynolds number of less than 2000 with a boundary layer thickness that is greater than one-half the thickness of the channels, and the output channel, the input channel, and the heating channel all being integrated portions of a heat exchanger; and
transferring heat between the output channel and the input channel, the input channel and the output channel each having a plate-like layout in which the width of the channel is at least ten times the thickness of the channel, the thickness of the channel extending between shared walls of the input channel and the output channel and the input channels alternate with the output channels in a side-to-side relationship with support elements within at least some of the input channels and output channels.

26. The method of heating a food product of claim 25, wherein the input channel and the output channel do not include a flow reversal section.

27. A method of sterilizing a liquid, comprising:
flowing a liquid through an input channel;
flowing the liquid through a heating channel that is fluidly coupled to the input channel, the heating channel including an actively heated zone wherein a heater provides thermal energy to the actively heated zone, the heater being integrated with the actively heated zone, the liquid being transiently heated to a predetermined temperature;
flowing the liquid through an output channel fluidly coupled to the heating channel, the output channel being adjacent the input channel, the input channels and the output channels are configured to induce liquid flow in the channel with a Reynolds number of less than 2000 with a boundary layer thickness that is greater than one-half the thickness of the channels, and the output channel, the input channel, and the heating channel all being integrated portions of a heat exchanger; and
transferring heat between the output channel and the input channel, the input channel and the output channel each having a plate-like layout in which the width of the channel is at least ten times the thickness of the channel, the thickness of the channel extending between shared walls of the input channel and the output channel and the input channels alternate with the output channels in a side-to-side relationship with support elements within at least some of the input channels and output channels.

28. The method of sterilizing a liquid of claim 27, wherein the input channel and the output channel do not include a flow reversal section.

29. The method of sterilizing a liquid of claim 27, wherein the liquid is a food product.

30. A method of heating a liquid, comprising:
flowing a liquid to be heated through an input channel;
receiving heat by the flowing liquid, the heat being received from an output channel;
flowing the liquid through a heating channel that is fluidly coupled to the input channel, the heating channel including an actively heated zone wherein a heater provides thermal energy to the actively heated zone, the heater being integrated with the actively heated zone, the liquid being heated to a predetermined temperature for at least a predetermined time; and
flowing the liquid through the output channel fluidly coupled to the heating channel, the output channel being adjacent the input channel, the input channels and the output channels are configured to induce liquid flow in the channel with a Reynolds number of less than 2000 with a boundary layer thickness that is greater than one-half the thickness of the channels,
wherein the input channel and the output channel are microchannels having a thickness less than 100 micrometers, the input channel and the output channel each having a plate-like layout in which the width of the channel is at least ten times the thickness of the channel, the thickness of the channel extending between shared walls of the input channel and the output channel and the input channels alternate with the output channels in a side-to-side relationship with support elements within at least some of the input channels and output channels.

31. The method of heating a liquid of claim 30, wherein the liquid is a food product.

32. The method of heating a liquid of claim 30, wherein the liquid is at least partially sterilized by the process.

33. The method of heating a liquid of claim 30, wherein the liquid includes a food product and the liquid is at least partially sterilized by the process.

34. A method of heating a liquid, comprising:
flowing a liquid to be heated through an input channel;
receiving heat by the flowing liquid, the heat being received from an output channel;
flowing the liquid through a heating channel that is fluidly coupled to the input channel, the heating channel including an actively heated zone wherein a heater provides thermal energy to the actively heated zone through a direct thermal coupling of the heater to the actively heated zone, the liquid being heated to a predetermined temperature for at least a predetermined time; and
flowing the liquid through the output channel fluidly coupled to the heating channel, the output channel being adjacent the input channel, the input channels and the output channels are configured to induce liquid flow in the channel with a Reynolds number of less than 2000 with a boundary layer thickness that is greater than one-half the thickness of the channels,
wherein the input channel and the output channel are configured such that the flow of the liquid has substantially laminar flow and the input channel and the output channel each having a plate-like layout in which the width of the channel is at least ten times the thickness of the channel, the thickness of the channel extending between shared walls of the input channel and the output channel and the input channels alternate with the output channels in a side-to-side relationship with support elements within at least some of the input channels and output channels.

35. The method of heating a liquid of claim 34, wherein the liquid is at least partially sterilized by the process.

36. The method of heating a liquid of claim 34, wherein the liquid includes a food product and the liquid is at least partially sterilized by the process.

* * * * *